United States Patent

Shimizu et al.

[11] Patent Number: 5,980,500
[45] Date of Patent: Nov. 9, 1999

[54] DISPOSABLE DIAPER

[75] Inventors: Shingo Shimizu; Yoshitaka Mishima, both of Kagawa-ken, Japan

[73] Assignee: Uni-Charm Corporation, Ehime-ken, Japan

[21] Appl. No.: 08/890,676

[22] Filed: Jul. 9, 1997

[30] Foreign Application Priority Data

Jul. 15, 1996 [JP] Japan .................................. 8-185098

[51] Int. Cl.$^6$ .................................................. A61F 13/15
[52] U.S. Cl. ...................................... 604/385.1; 604/358
[58] Field of Search .............................. 604/378, 385.1, 604/358

[56] References Cited

U.S. PATENT DOCUMENTS

| | | | |
|---|---|---|---|
| 4,430,088 | 2/1984 | Karami | 604/385.1 |
| 5,037,409 | 8/1991 | Chen et al. | 604/378 |
| 5,188,624 | 2/1993 | Young, Sr. et al. | 604/378 |
| 5,352,217 | 10/1994 | Curro | 604/378 |
| 5,429,629 | 7/1995 | Latimer et al. | 604/378 |
| 5,458,592 | 10/1995 | Abuto et al. | 604/385.1 |

*Primary Examiner*—John G. Weiss
*Assistant Examiner*—Dennis Ruhl
*Attorney, Agent, or Firm*—Lowe Hauptman Gopstein Gilman & Berner

[57] ABSTRACT

A disposable diaper including a liquid-absorbent pad including an absorptive core and upper and lower absorptive sheets covering upper and lower surfaces of the absorptive core, respectively. The upper and lower absorptive sheets are bonded to the upper and lower surfaces of the absorptive core by means of adhesive applied on respective inner surfaces of the upper and lower absorptive sheets, and bonded to each other by means of the same adhesive at their portions extending outward beyond longitudinally opposite ends and transversely opposite side edges of the absorptive core. The adhesive describes spirals extending longitudinally of the diaper and these spirals on upper and lower absorptive sheets transversely alternate and each pair of adjacent spirals overlap each other at their transversely opposite side edges except in the proximities of their axes.

5 Claims, 2 Drawing Sheets

DISPOSABLE DIAPER

BACKGROUND OF THE INVENTION

This invention relates generally to disposable diapers, and more particularly to disposable diapers such as infant and adult diapers for the absorption and containment of urine and other body exudates.

It is well known to make a liquid-absorbent pad disposed between a topsheet and a backsheet of a disposable diaper by covering upper and lower surfaces of an absorptive core, made of fluff pulp, for example, with upper and lower absorptive sheets such as tissue sheets. It is also well known to bond these absorptive sheets to the surfaces of the absorptive core by means of adhesive agent such as hot melt adhesive. The adhesive has conventionally been applied on respective inner surfaces of these absorptive sheets in the form of a plurality of lines extending in parallel to one another or a plurality of spots. By covering the absorptive core in this manner, fluff pulp is prevented from scattering in the course of production to avoid wasteful use of material and improve productivity.

However, the conventional manner of adhesive application as in the above-mentioned well known art makes it difficult to seal the absorptive core around it with the upper and lower absorptive sheets and sometimes undesirable leakage of the absorptive core material occurs through gaps of the upper and lower absorptive sheets during a process of production. To avoid this, separate adhesive exclusively for sealing purpose must be applied to portions of the sheets around the absorptive core. As a result, in addition to the adhesive used to bond the sheets to the absorptive core, the adhesive used to seal the absorptive core will be applied to the sheets. This leads to unacceptably high rigidity of the sheets which irritates the wearer's skin and degrades comfort. While it is possible to assign the respective adhesives to different regions, the equipment for production will be inevitably complicated and a cost of the product will be correspondingly increased.

SUMMARY OF THE INVENTION

In view of the problem as described above, it is a principal object of the invention to provide disposable diapers provided with a liquid-absorbent pad contributing to simplification of the manufacturing process and improved comfort a in wearing the diaper.

The object set forth above is achieved, according to the invention, by a disposable diaper comprising a liquid-permeable topsheet, a liquid-impermeable backsheet and a liquid-absorbent pad disposed between these two sheets and including an absorptive core formed from at least fluff pulp of 40~100% by weight:

The absorptive core is elongated in the longitudinal direction of the diaper and has upper and lower surfaces thereof covered with upper and lower absorptive sheets, respectively. The upper and lower absorptive sheets are bonded to the upper and lower surfaces of the absorptive core, respectively, by means of a plural lines of adhesive applied on respective inner surfaces of the upper and lower absorptive sheets so as to describe spirals extending in the longitudinal direction and transversely spaced apart from one another by a predetermined distance, and bonded to each other by the spirals of adhesive at portions extending outward beyond longitudinally opposite ends as well as transversely opposite side edges of the absorptive core. The upper and lower absorptive sheets are placed so that, when these two sheets are put one upon another with interposition of the absorptive core, said spirals of adhesive applied on these two sheets are alternately arranged transversely of the diaper and each pair of adjacent spirals overlap each other at their transversely opposite side edges except in the proximity of their axes of intersection.

With the disposable diaper provided by the invention, the adhesives applied on the respective inner surfaces of the upper and lower tissue sheets covering the absorptive core of the absorbent pad describe the spirals extending longitudinally of the diaper. When these two sheets are put one upon another, the spirals are alternately arranged and each pair of adjacent spirals overlap each other along their transversely opposite sides except their portions in the proximity of their axes. The upper and lower sheets are bonded to each other in sealed relationship by the spirals of adhesive applied on these two sheets at their portions extending outward beyond the longitudinally opposite ends of the absorptive core and bonded to each other in sealed relationship by the spirals of the adhesive applied on one of these two sheets at their portions extending outward beyond the transversely opposite side edges of the absorptive core. This manner of adhesive application is effective to reduce product cost since no separately provided equipment is necessary to bond the upper and lower sheets to each other in sealed relationship along their portions extending outward beyond the peripheral edge of the absorptive core. Furthermore, it is unnecessary to use a large amount of adhesive at the longitudinally opposite ends as well as the transversely opposite side edges of the upper and lower tissue sheets and consequently there is no apprehension that these portions might have unacceptably high rigidity due to the adhesive.

Other and further objects, features and advantages of the invention will appear more fully from the following description.

DESCRIPTION OF THE PREFERRED EMBODIMENT

Figure 1:
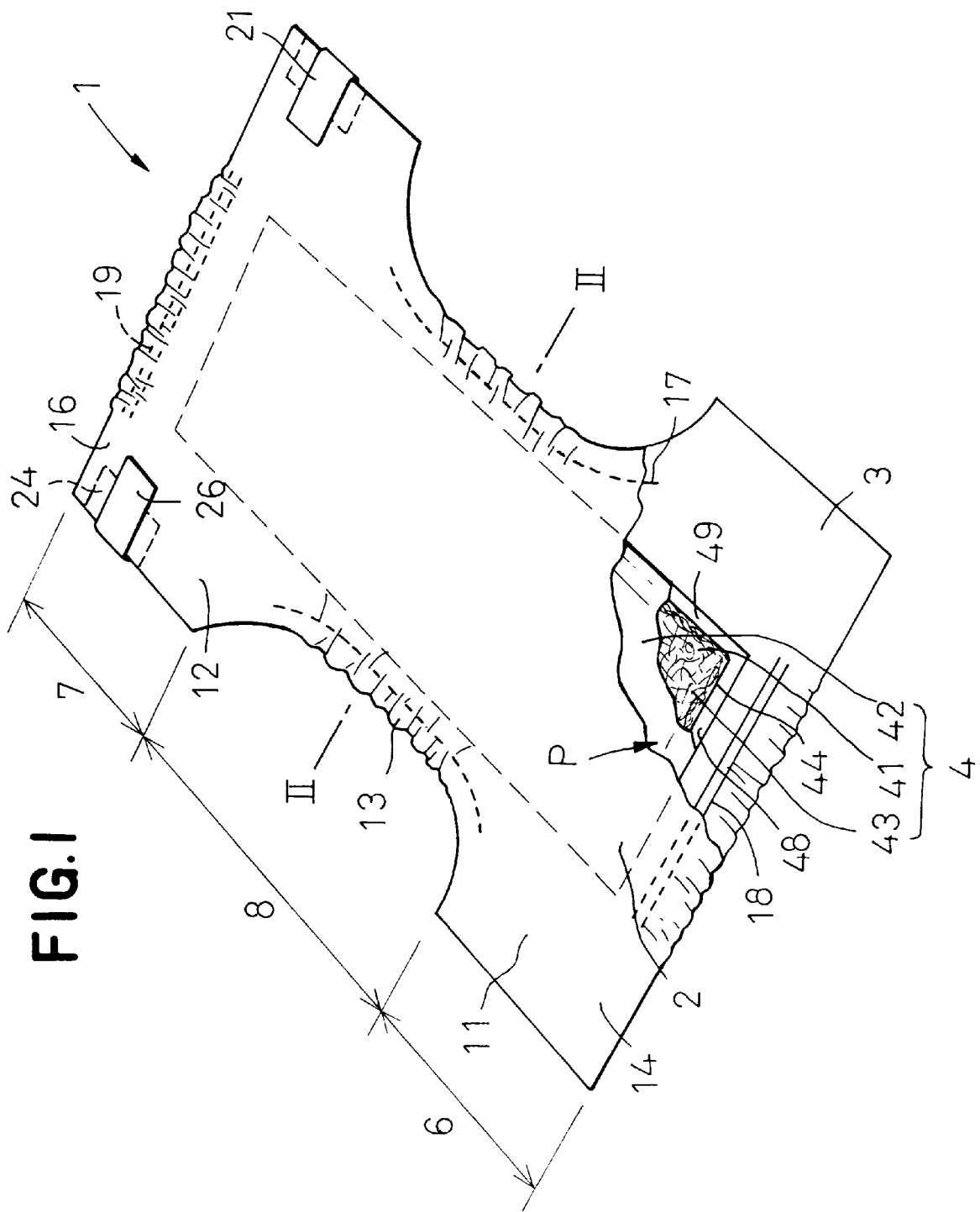
FIG. 1 is a perspective view of a disposable diaper according to the invention as partially broken away.

Disposable diaper 1 shown by FIG. 1 in a perspective view as partially broken away comprises a liquid-permeable topsheet 2, a liquid-impermeable backsheet 3 and a liquid-absorbent pad 4, and these components form a front waist region 6, a rear waist region 7 and a crotch region 8 extending between these two waist regions 6, 7 as viewed in the longitudinal direction. The topsheet 2 and the backsheet 3 are bonded to each other along their portions extending outward beyond a peripheral edge of the absorbent pad 4 to define transversely opposite side edges 11, 12 of the front and rear waist regions 6, 7, respectively, transversely opposite side edges 13 of the crotch region 8 defining respective leg-openings, and longitudinal ends 14, 16 of the front waist region 6 and the rear waist region 7, respectively, together defining a waist-opening. The leg-opening defining the side edges 13 and the longitudinal ends 14, 16 are provided with leg-opening elastic members 17 and waist-opening elastic members 18, 19. These elastic members 17, 18, 19 are secured in their longitudinally extended conditions to the inner surface(s) of the topsheet 2 and/or the backsheet 3. The rear waist region 7 is provided on its transversely opposite side edges 12 with laterally extendible tape fasteners 21, respectively. These tape fasteners 21 comprises distal end portions 26 folded back onto the inner side of the diaper 1 so as to be extendable outward and proximal end portions 24 secured to the diaper.

In the diaper 1, the topsheet 2 is formed by a nonwoven fabric of thermally meltable synthetic resin such as a polypropylene or perforated film and the backsheet 3 is formed by a film of thermally meltable synthetic resin such as polyethylene and polypropylene. The distal end portion 26 and the proximal end portion 24 of the tape fastener 21 are made of a nonwoven fabric and/or film obtained from thermally meltable synthetic resin such as polypropylene and a fastening zone is formed on the inner surface of the distal end portion 26.

Figure 2:
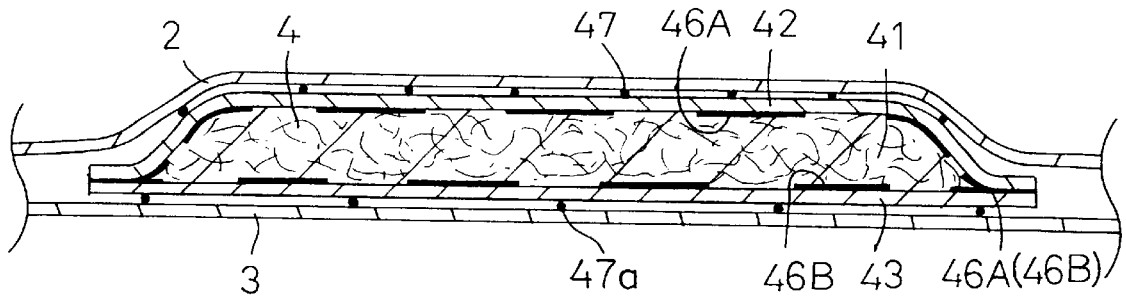
FIG. 2 is a sectional view of a liquid-absorbent pad taken along line II—II in FIG. 1.

FIG. 2 is a sectional view of the liquid-absorbent pad 4 taken along line II—II in FIG. 1. The absorbent pad 4 comprises an absorptive core 41 formed by a mixture of fluff pulp of 40~100% by weight, liquid-absorptive polymer particles of 0~45% by weight and thermoplastic synthetic fibers of 0~20% by weight, and upper and lower tissue sheets 42, 43 covering upper and lower surfaces of the absorptive core 41. The upper and lower tissue sheets 42, 43 are bonded to each other by means of first and second hot melt adhesives 46A, 46B as will be described later along their portions extending outward beyond longitudinally opposite ends (only the front end 44 is shown in FIG. 1) as well as beyond transversely opposite side edges (not shown) of the absorptive core 41. The upper and lower tissue sheets 42, 43 are also bonded to the upper and lower surfaces of the absorptive core 41, respectively, by means of the first and second hot melt adhesives 46A, 46B. The upper tissue sheet 42 is bonded to the inner surface of the topsheet 2 by means of third hot melt adhesive 47 and the lower tissue sheet 43 is bonded to the inner surface of the backsheet 3 by means of fourth hot melt adhesive 47A.

Figure 3:
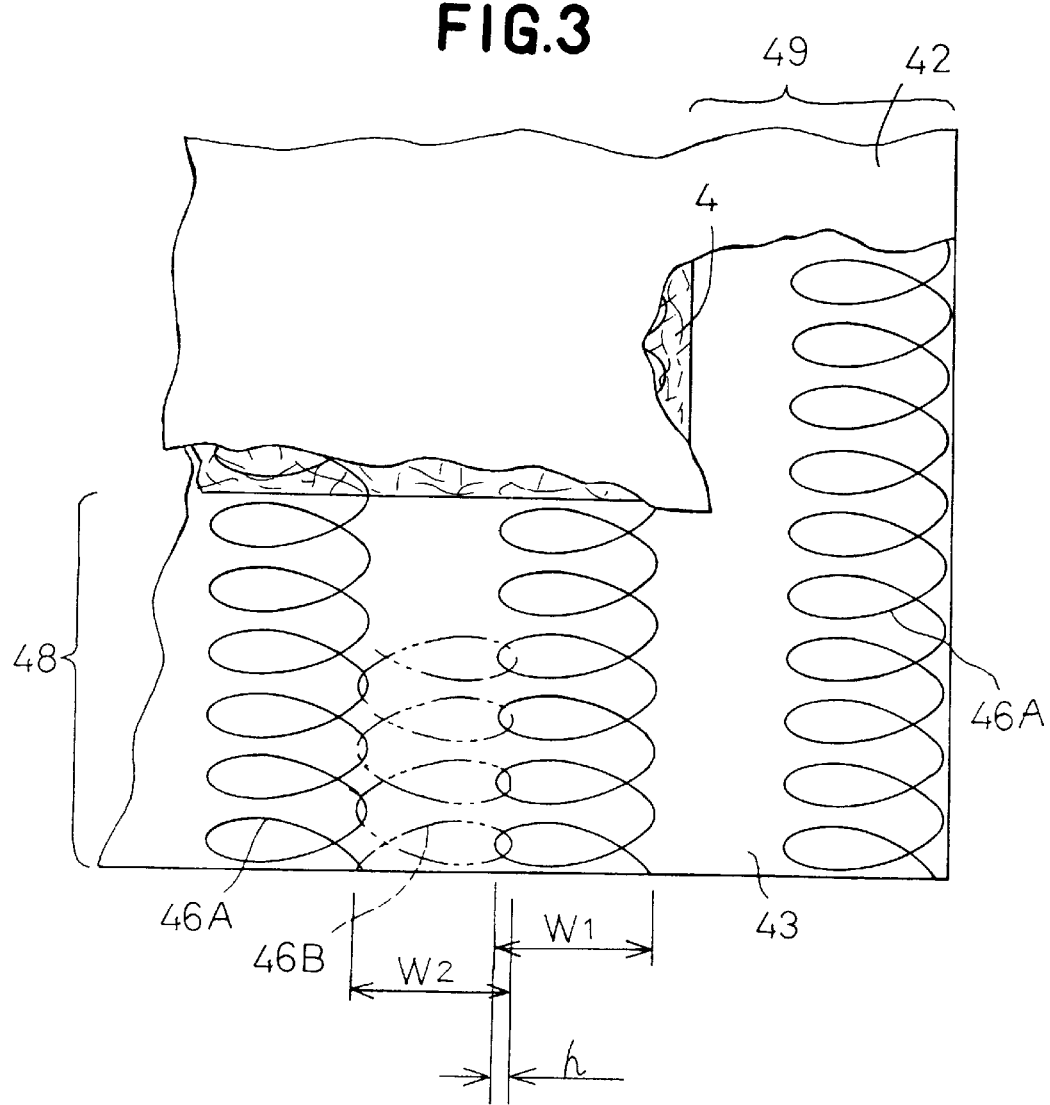
FIG. 3 is a plan view showing an application pattern of adhesives as viewed in a direction indicated by an arrow P in FIG. 1.

FIG. 3 is a plan view partially showing an application pattern of the first and second hot melt adhesives 46A, 46B as viewed in a direction indicated by an arrow P. The first hot melt adhesive 46A is applied on the inner surface of the upper tissue sheet 42 and the second hot melt adhesive 46B indicated by imaginary lines so as to be distinguished from the first hot melt adhesive 46A is applied on the inner surface of the lower tissue sheet 43 in counterclockwise and clockwise spirals of a predetermined pitch, respectively. The spirals described by the respective adhesives 46A, 46B respectively have widths $W_1$ and $W_2$ and overlap each other except their zones adjacent their axes. A width of such overlapping is designated by h. Being applied in this manner, the first and second hot melt adhesives 46A, 46B serve to maintain the portions 48 (FIG. 1) of the upper and lower tissue sheets 42, 43 extending beyond the longitudinally opposite ends of the absorptive core 41 and put one upon another in sealed relationship, on the one hand, and the portions 49 (FIG. 1) of the upper and lower tissue sheets 42, 43 extending outward beyond transversely opposite side edges of the absorptive core 41 and put one upon another are also maintained in sealed relationship by the spirals of the first or second hot melt adhesive 46A or 46B. The first and second hot melt adhesives 46A, 46B spirally applied on the upper and lower tissue sheets 42, 43, respectively, slightly overlap at the portions 48, 49 of these two tissue sheets put one upon another as well as at the portions thereof in the proximity of the longitudinally opposite ends of the absorptive core 41. This unique manner in which the upper and lower tissue sheets 42, 43 are bonded to each other eliminates the demand for equipment which otherwise would be separately provided to bond these two sheets 42, 43 to each other in sealed relationship at the longitudinally opposite ends as well as the transversely opposite side edges thereof. In addition, an amount of the adhesives to be applied on these ends and side edges is, at most, equal to an amount of the adhesives which otherwise would be applied on any one of these two sheets 42, 43. Accordingly, the diaper 1 of the invention is not only economical from the viewpoint of eliminating the equipment for application of adhesives and the amount of the adhesive to be consumed but also advantageously prevents the longitudinally opposite ends and the transversely opposite side edges of the absorbent pad 4 from having a rigidity unacceptably increased due to use of a large amount of the adhesives.

The entire disclosure of Japanese Patent Application No. 8-185098 filed on Jul. 15, 1996 including specification, claims, drawings and abstract are incorporated herein by reference in its entirety.

Having described our invention as related to the embodiment shown in the accompanying drawings, it is our intention that the invention be not limited by any of the details of description, unless otherwise specified, but rather be construed broadly within its spirit and scope as set out in the accompanying claims.

What is claimed is:

1. A disposable diaper comprising a liquid-permeable topsheet, a liquid-impermeable backsheet and a liquid-absorbent pad disposed between said topsheet and backsheet and including an absorptive core, wherein:

said absorptive core is elongated in the longitudinal direction of said diaper and has upper and lower surfaces thereof covered with upper and lower absorptive sheets, respectively;

said upper and lower absorptive sheets are bonded to said upper and lower surfaces of said absorptive core, respectively by means of a plural lines of adhesive applied on respective inner surfaces of said upper and lower absorptive sheets so as to form spirals extending in said longitudinal direction and transversely spaced apart from one another by a predetermined distance, said upper and lower absorptive sheets being bonded to each other by said spirals of adhesive at portions extending outward beyond longitudinally opposite ends as well as transversely opposite side edges of said absorptive core; and wherein said upper and lower absorptive sheets are positioned so that, when said upper and lower absorptive sheets are put one upon another with said absorptive core therebetween, said spirals of adhesive applied on said upper and lower absorptive sheets are alternately arranged transversely of said diaper and each pair of adjacent spirals overlap each other at transversely opposite side edges thereof except in the proximities of their axes of intersection; and wherein individual loops of some of the spirals extend in the transverse direction of the diaper with a portion of the spiral connecting to longitudinally adjacent loops intersecting a corresponding portion of the transversely adjacent spiral.

2. The disposable diaper according to claim 1, wherein said upper and lower absorptive sheets are made of tissue paper.

3. The disposable diaper according to claim 1, wherein said absorptive core further includes liquid-absorptive polymer particles.

4. The disposable diaper according to claim 1, wherein said adhesive is hot melt adhesive.

5. The diaper of claim 1, wherein sad absorptive core is formed from at least fluff pulp 40~100% by weight.

* * * * *

(12) EX PARTE REEXAMINATION CERTIFICATE (4923rd)
United States Patent
Shimizu et al.

(10) Number: US 5,980,500 C1
(45) Certificate Issued: Mar. 30, 2004

(54) DISPOSABLE DIAPER

(75) Inventors: Shingo Shimizu, Kagawa-ken (JP);
Yoshitaka Mishima, Kagawa-ken (JP)

(73) Assignee: Uni-Charm Corporation, Kawanoe (JP)

Reexamination Request:
No. 90/006,439, Oct. 29, 2002

Reexamination Certificate for:
Patent No.: 5,980,500
Issued: Nov. 9, 1999
Appl. No.: 08/890,676
Filed: Jul. 9, 1997

(30) Foreign Application Priority Data

Jul. 15, 1996 (JP) .............................................. 8-185098

(51) Int. Cl.$^7$ ................................................. A61F 13/15
(52) U.S. Cl. ................................... 604/385.01; 604/358
(58) Field of Search .......................... 604/358–383.01, 604/385.23

(56) References Cited

U.S. PATENT DOCUMENTS 4,699,823 A * 10/1987 Kellenberger et al. ...... 428/219
4,704,115 A * 11/1987 Buell ..................... 604/385.26
5,342,647 A    8/1994 Heindel et al.

FOREIGN PATENT DOCUMENTS

GB    2252047    7/1992
GB    2255720    11/1992

* cited by examiner

*Primary Examiner*—Kim M. Lewis

(57) ABSTRACT

A disposable diaper including a liquid-absorbent pad including an absorptive core and upper and lower absorptive sheets covering upper and lower surfaces of the absorptive core, respectively. The upper and lower absorptive sheets are bonded to the upper and lower surfaces of the absorptive core by means of adhesive applied on respective inner surfaces of the upper and lower absorptive sheets, and bonded to each other by means of the same adhesive at their portions extending outward beyond longitudinally opposite ends and transversely opposite side edges of the absorptive core. The adhesive describes spirals extending longitudinally of the diaper and these spirals on upper and lower absorptive sheets transversely alternate and each pair of adjacent spirals overlap each other at their transversely opposite side edges except in the proximities of their axes.

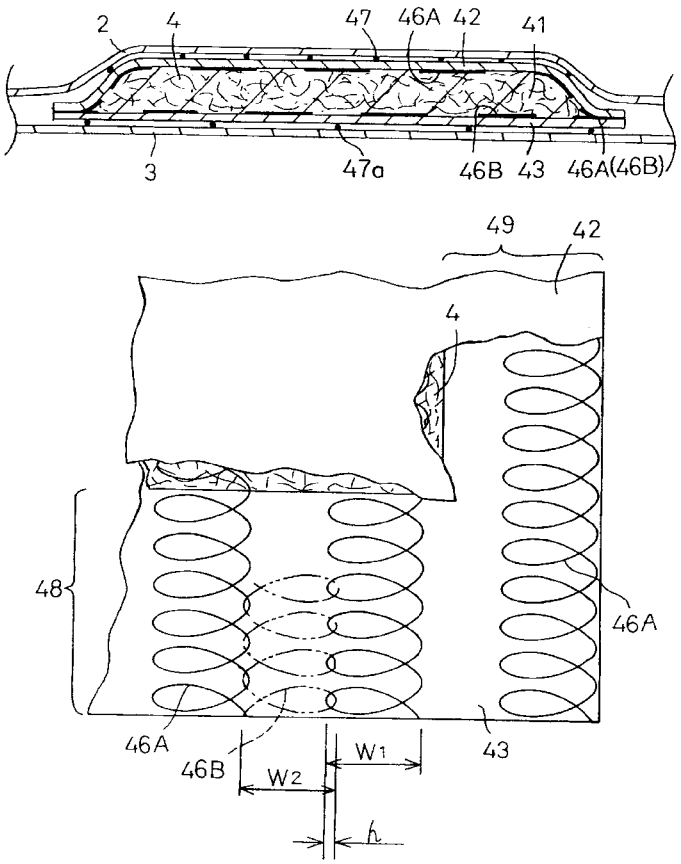

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–5 is confirmed.

New claims 6 and 7 are added and determined to be patentable.

*6. The diaper of claim 1, wherein the spirals of adhesive are applied on the inner surfaces of the upper and lower absorptive sheets in opposite spiral directions.*

*7. The diaper of claim 1, wherein the spirals of adhesive applied on the inner surfaces of the upper and lower absorptive sheets are counterclockwise and clockwise spirals, respectively.*

* * * * *